United States Patent [19]

Daniel et al.

[11] 4,358,388

[45] Nov. 9, 1982

[54] MAGNETIC POLYMER LATEX AND PREPARATION PROCESS

[75] Inventors: Jean-Claude Daniel, Fontenay/Sous/Bois; Jean-Luc Schuppiser, Claye-Souilly, both of France; Marc Tricot, deceased, late of Andilly, France, by Nicole Tricot, heir

[73] Assignee: Rhone Poulenc Industries, Paris, France

[21] Appl. No.: 254,778

[22] Filed: Apr. 16, 1981

[30] Foreign Application Priority Data

Apr. 18, 1980 [FR] France ................. 80 08696

[51] Int. Cl.$^3$ ................. H01F 1/00; H01F 1/26
[52] U.S. Cl. ................. 252/62.54
[58] Field of Search ................. 252/62.53, 62.54

[56] References Cited

U.S. PATENT DOCUMENTS

| | | | |
|---|---|---|---|
| 3,149,996 | 9/1964 | Wagner et al. | 252/62.54 X |
| 3,228,881 | 1/1966 | Thomas | 252/62.54 |
| 3,471,415 | 10/1969 | Friedman | 252/62.54 X |
| 3,725,285 | 4/1973 | Denk et al. | 252/62.54 |
| 4,002,804 | 1/1977 | Akashi et al. | 428/539 |

*Primary Examiner*—F. Edmundson
*Attorney, Agent, or Firm*—Finnegan, Henderson, Farabow, Garrett & Dunner

[57] ABSTRACT

Magnetic-polymer latex having a concentration of less than 65% by weight of hydrophobic vinyl aromatic polymer particles. The polymer particles have diameters from 0.03 to 5 microns and also have dispersed therein a magnetically-charged material in an amount of from 0.5 to 50% by weight with respect to the polymer portion of the polymer particles.

A process for preparing magnetic-polymer latices. Magnetically charged particles are dispersed in an organic phase comprising an organically soluble initiator and an organic monomeric component selected from the group consisting of a single vinyl aromatic monomer and a combination of a single vinyl aromatic monomer and a copolymerizing monomer. The dispersion so obtained is mixed with an aqueous solution containing an emulsifying agent and the mixture is homogenized. Polymerization is then effected to form a magnetic-polymer latex containing hydrophobic vinyl aromatic polymer particle. More organic monomer component may be added immediately prior to or during polymerization. Alternatively, the magnetically-charged material may be dispersed into an organic phase comprising an organically soluble initiator and a water-soluble organic compound. An organic monomeric component is added to the aqueous-organic phase mixture after homogenization and prior to or during polymerization, which is effected to form a magnetic-polymer latex containing hydrophobic polymer particles. The magnetic-polymer latices obtained are useful in paints, magnetic tapes, recordings, and biological applications.

22 Claims, No Drawings

MAGNETIC POLYMER LATEX AND PREPARATION PROCESS

BACKGROUND OF THE INVENTION

This invention relates to polymer latices containing magnetically-charged material and to processes for preparing polymer latices containing magnetically-charged material.

Magnetic polymers in the form of gels or particles are generally obtained by mixing a magnetically-charged material into a polymer prepared by conventional bulk, solution, emulsion or suspension polymerization methods. In the preparation of magnetic polymers, however, an additional stage, such as atomization, coagulation, extrusion and distillation of the solvent is often required, thus necessitating both suitable equipment and the expenditure of more than trivial energy. Further, in preparing magnetic polymers, workers often encounter dispersion difficulties, resulting in polymer particles having both defective magnetic charge distributions and modified properties.

Although mixing a magnetically-charged material into a polymer latex is also known, special polymers have heretofore been required to disperse the magnetic charge. The products obtained, moreover, often lack adequate stability.

To overcome these problems, workers have suggested addition of a magnetically-charged material during the emulsion polymerization of a mixture of monomers, at least one of which is water-soluble. Disadvantageously, however, hydrophilic polymers of restricted applicability are formed.

Moreover, addition of a magnetically-charged material during the emulsion polymerization of water-insoluble monomers produces unsatisfactory results because the magnetically-charged material fails to be incorporated into the polymer particles during polymerization.

SUMMARY OF THE INVENTION

The present invention overcomes the problems and disadvantages of the prior art by providing magnetic polymer latices which (1) are stable; (2) comprise polymer particles containing therein well-dispersed magnetically-charged materials; and, (3) are easily obtained by polymerizing water-insoluble monomers in the presence of a magnetically-charged material. Therefore, an object of the invention is to produce stable magnetic polymer latices. Another object of the present invention is to produce magnetic polymer latices comprising polymer particles which contain therein well-dispersed magnetically-charged materials. A further object of the present invention is to provide magnetic polymer latices which are easily obtained by polymerizing water-insoluble monomers in the presence of a magnetically-charged material.

Additional objects and advantages of the invention will be set forth in part in the description which follows, and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the invention as embodied and described herein, the magnetic polymer latices of this invention comprise:

(a) less than 65% by weight of hydrophobic vinyl aromatic polymer particles having a mean diameter between 0.03 and 5 microns; and (b) a magnetically-charged material in an amount from 0.5 to 50% by weight with respect to the polymer portion of the particles, the magnetically charged material being dispersed within the polymer particles.

To further achieve the objects and in accordance with the purpose of the invention, as embodied and described herein, the process of this invention for preparing the above-described magnetic polymer latex comprises the steps of:

(a) dispersing a magnetically-charged material into an organic phase comprising an organically-soluble initiator and an organic monomeric component selected from the group consisting of a single vinyl aromatic monomer and a combination of a single vinyl aromatic monomer and a copolymerizing monomer;

(b) preparing an aqueous solution comprising water and at least one emulsifier;

(c) mixing the organic phase containing the dispersed magnetically-charged material with the prepared aqueous solution;

(d) homogenizing the mixture of the organic phase containing the dispersed magnetically-charged material and the prepared aqueous solution; and (e) polymerizing the homogenized mixture to obtain a magnetic-polymer latex containing hydrophobic vinyl aromatic polymer particles.

To further achieve the objects and in accordance with the purpose of the invention, as embodied and described herein, the process of this invention for preparing the above-described magnetic polymer latex comprises the steps of:

(a) dispersing a magnetically-charged material into an organic phase comprising an organically-soluble initiator and a water-insoluble organic compound;

(b) preparing an aqueous solution comprising water and at least one emulsifier;

(c) mixing the organic phase containing the dispersed magnetically-charged material with the prepared aqueous solution;

(d) homogenizing the mixture of the organic phase containing the dispersed magnetically-charged material and the prepared aqueous solution;

(e) adding to the homogenized mixture an organic monomeric component selected from the group consisting of a single vinyl aromatic monomer and a combination of a single vinyl aromatic monomer and a copolymerizing monomer; and (f) polymerizing the homogenized mixture after the addition of the organic monomeric component, to obtain a magnetic-polymer latex containing hydrophobic vinyl aromatic polymer particles.

DETAILED DESCRIPTION OF THE PREFERRED EMBODIMENTS

Reference will now be made in detail to the presently preferred embodiments of the invention.

In accordance with the invention, the magnetic polymer latex comprises less than 65% by weight of hydrophobic vinyl aromatic polymer particles having a mean diameter between 0.03 and 5 microns. Suitable hydrophobic vinyl aromatic polymers include (a) homopolymers of water-insoluble vinyl aromatic monomers, such as styrene, alpha-methylstyrene, ethylstyrene, tert-butylstyrene, and vinyltoluene; (b) copolymers consisting of water-insoluble vinyl aromatic monomers such as styrene, alpha-methylstyrene, ethylstyrene, tert-butylstyrene and vinyltoluene; and (c) copolymers consisting of at least one water-insoluble vinyl aromatic monomer, such as styrene, alpha-methylstyrene, ethylstyrene, tert-butylstyrene, and vinyltoluene, and at least one other water-insoluble copolymerizing monomer, such as a diene compound, an alkyl acrylate, an alkyl methacrylate, an ester of ethylenic acid and alkyl.

Preferably, the alkyl groups of the alkyl acrylates and alkyl methacrylates comprise from 3 to 10 carbon atoms, the ethylenic acid of the esters comprise 4 or 5 carbon atoms and the alkyl group of the esters comprise 1 to 8 carbon atoms. Suitable esters include heptyl fumarate, octyl fumarate, methyl itaconate and ethyl itaconate. Suitable diene compounds include butadiene and isoprene.

When the hydrophobic vinyl aromatic polymers are copolymers (c) consisting of at least one water-insoluble vinyl aromatic monomer and at least one other copolymerizing monomer, the copolymerizing monomer may be present in up to equal amounts of the vinyl aromatic monomer.

Preferably, the polymer particle concentration in the magnetic-polymer latex is between 5 and 50% by weight. The latex, however, may be diluted or concentrated without causing problems.

Preferably, the mean particle diameter of the polymer particles is between 0.05 and 1 micron. The polymer particles have a wide or narrow granulometric distribution depending on the polymerization conditions implemented in the formation of the polymer, as described below. Moreover, the particles are attracted by a magnet even when the concentration of polymer particles in the latex is as low as 1% by weight.

In accordance with the invention, the magnetic-polymer latex further comprises a magnetically-charged material in an amount from 0.5 to 50% by weight with respect to the polymer portion of the polymer particles, the magnetically-charged material being dispersed within the polymer particles. Dispersion of the magnetically-charged material within the polymer particles gives the particles a magnetic charge.

Preferably, the magnetically-charged material represents from 0.5 to 35% by weight with respect to the polymer portion of the polymer particles. Most preferably, the magnetically-charged material represents from 0.7 to 20% by weight with respect to the polymer portion of the polymer particles.

The magnetically-charged material dispersed within the polymer particles is in the form of particles sufficiently fine to be dispersed within the polymer particles. The magnetically-charge material particles generally have a size less than 1 micron. Preferably, the magnetically-charged material have a size between 0.002 and 0.05 microns.

Preferably, the magnetically-charged material is selected from the group consisting of a metal, metal alloy, iron oxide, chromium dioxide and iron oxide combined or mixed with a metal oxide selected from the group consisting of cobalt oxide, manganese oxide, zinc oxide, barium oxide and rare earth oxides. Suitable magnetically-charge materials include:

(1) metals, such as iron, iron-silicon, nickel, and cobalt
(2) metal alloys of any one of iron, iron-silicon, nickel or cobalt with at least one of molybdenum, chromium, copper, vanadium, manganese, aluminum and titanium;
(3) pure iron oxides, such as $Fe_3O_4$ or gamma-$Fe_2O_3$;
(4) iron oxides, such as $Fe_3O_4$ or gamma-$Fe_2O_3$ combined or mixed with other metal oxides such as cobalt oxide, manganese oxide, zinc oxide, barium oxide, and rare earth oxides; and
(5) chromium dioxide.

To produce the above-mentioned magnetic polymer latices, in accordance with the invention, the above-described magnetically-charged materials are dispersed into an organic phase. In a preferred embodiment of the invention, the organic phase comprises an organically-soluble initiator and an organic monomeric component selected from the group consisting of a single vinyl aromatic monomer and a combination of a single vinyl aromatic monomer and copolymerizing monomer.

Suitable initiators, either used alone or as mixtures of initiators, in amounts ranging from 0.1 to 10% by weight with respect to the organic monomeric component include such conventional organically soluble polymerization initiators as the azonitriles, such as azobisisobutyronitrile and azobiscyclohexane carbonitrile; the peroxides, such as benzoyl peroxide, dicumyl peroxide, ditert-butyl peroxide, diacetyl peroxide, dioctanyl peroxide, lauroyl peroxide, methylethylketone peroxide, caprylyl peroxide, dichloro-2,4-benzoyl peroxide, and parachlorobenzoyl peroxide; the tert-butyl perpivalate; the tert-butyl diethylperacetate; the tert-butyl perbenzoate; the ditert-butyl diperphthalate; and the 1,1-ditert-butyl-peroxide-3,3,5-trimethylcyclohexane.

The initiator must be dissolved in the organic phase prior to the homogenizing step. In some cases, to facilitate dissolution of the initiator in the organic phase, the initiator may advantageously be dissolved in a small amount of an organic solvent which, although miscible in the organic phase, will not inhibit polymerization. Suitable organic solvents include halogenated or non-halogenated aliphatic or aromatic hydrocarbons having less than 10 carbon atoms, such as methylene chloride, chloroform, carbon tetrachloride, dichloroethane, benzene and chlorobenzene.

Suitable organic monomeric components are monomers which result in hydrophobic polymers. Specifically, suitable water-insoluble vinyl aromatic monomers include styrene, alphamethylstyrene, ethylstyrene, tert-butyl styrene and vinyltoluene.

Suitable water insoluble copolymerizing monomers include the vinyl aromatic monomers described in the preceding paragraph used in all proportions; diene compounds, alkyl acrylates, alkyl methacrylates, esters of ethylenic acid and alkyl used in quantities of up to 50% by weight relative to the monomers. Preferably, the alkyl groups of the alkyl acrylates and alkyl methacrylates comprise from 3 to 10 carbon atoms, the ethylenic acid of the esters comprise 4 or 5 carbon atoms and the alkyl group of the esters comprise 1 to 8 carbon atoms. Suitable esters include heptyl fumarate, octyl fumarate, methyl itaconate and ethyl itaconate. Suitable diene compounds include butadiene and isoprene.

In accordance with the invention, the amount of magnetically-charged material dispersed into the organic phase is between 0.5 and 50% preferably between 0.5 and 35% and most preferably between 0.7 and 20% by weight with respect to the organic monomeric component.

Depending on the ultimately desired polymer, the organic phase may further include a crosslinking monomer in an amount between 0 and 5% by weight with respect to the organic monomeric component. Suitable crosslinking monomers include divinylbenzene, vinyl methacrylate, the acrylates or methacrylates of mono- or polyakylene (2-4 carbon atoms) glycol, triallyl cyanurate, and condensates of unsaturated carboxylic acid and polyol, such as the acrylate or methacrylate of trimethylol propane.

The organic phase may further include either in combination with a crosslinking monomer or by itself, a chain-limiting agent in an amount between 0 and 5% by weight with respect to the organic monomeric component. Suitable chain-limiting agents include alpha-methylstyrene dimer, the straight or branched chain alkylmercaptans, and the halogenated hydrocarbons.

The organic phase may further include a water-insoluble organic compound. The water-insoluble organic compound must be miscible with the organic monomeric component and must not inhibit polymerization. Preferably, the water-insoluble organic compound is also miscible with the initiator.

Suitable water-insoluble organic compounds include: saturated and unsaturated aliphatic, alicyclic and aromatic hydrocarbons, which may be halogenated and which also have 10 to 30 carbon atoms, such as dodecane, hexadecane, heptadecane, eicosane, paraffin waxes, chlorinated paraffins, decene-1, do-decene-1, tetra-decene-1, hexa-decene-1, hepta-decene-1, octa-decene-1, eicosene-1, tetraethylbenzene, hexaethylbenzene, naphthalene, and anthracene; saturated or unsaturated aliphatic alcohols comprising 10 to 30 carbon atoms, such as lauric alcohol, myristic alcohol, cetylic alcohol, stearylic alcohol, eicosylic alcohol, and oleic alcohol; esters of mineral acid or organic acid having 1 to 20 carbon atoms and alcohol having 1 to 20 carbon atoms, the esters having at least 10 carbon atoms, such as tricresyl phosphate, cetyl formate, stearyl formate, dioctyl adipate, dibutyl sebacate, propyl laurate, ethylhexyl laurate, ethyl palmitate, dioctyl phthalate, diethylhexyl phthalate, dicyclohexyl phthalate, and dibenzyl phthalate; and low molecular-weight polymers, such as liquid polybutadienes, polyethylene oils and waxes. The amount of water-insoluble organic compound to be used may represent up to 50% and preferably up to 20% by weight of the totality of the organic phase containing the magnetic charge.

Prior to being dispersed into the organic phase, the magnetically-charged material may be advantageously dispersed into all or part of the water-insoluble organic compound and/or an organic solvent selected from those described above as suitable solvents for the organically-soluble initiators.

As will be explained in further detail below, the invention may be practiced without any or all of the organic monomeric component ultimately to be polymerized being present in the organic phase into which the magnetically-charged material is dispersed. If less than all of the organic monomeric component ultimately to be polymerized is included in the organic phase, the organic phase constitutes at least 1% of the totality of the organic phase.

In accordance with the invention, an aqueous solution is prepared comprising water and at least one emulsifier, which is dissolved in the water. Depending on the type of organic monomeric compound and emulsifier involved in a particular system, a buffer may also be present.

Suitable emulsifiers, chosen to ensure the stability of the reaction medium and of the latex to be produced, may be anionic, cationic and/or non-ionic. Preferably the emulsifiers are present in quantities between 0.1 and 5% by weight with respect to the organic phase containing the magnetic charge.

Suitable anionic emulsifiers include fatty acid salts; alkalimetal alkylsulfates, alkylsulfonates, alkylarylsulfonates, alkylsulfosuccinates, alkylphosphates; alkyl sulfosuccinates; sulfonates of alkylphenol-polyglycol ethers; salts of alkylsulfopolycarboxylic acid esters; condensation products of fatty acids with the oxy- and amino-alkanesulfonic acids; sulfated derivatives of the polyglycol ethers; sulfated esters of fatty acids and polyglycols; and sulfated fatty acid alkanolamides.

Suitable cationic emulsifiers include alkylamides and their water-soluble salts, and soluble salts of the alkylamines N-substituted by alkyl and/or alkylaryl and/or hydroxyalkyl radicals.

Suitable non-ionic emulsifiers include fatty esters of polyalcohols, fatty acid alkanolamides, ethylene polyoxides, copolyoxides of ethylene and propylene and oxyethylenated alkylphenols.

In accordance with the invention, the organic phase containing the dispersed magnetically-charged material is mixed with the prepared aqueous solution. Thus, a dispersion of organic phase in the aqueous solution is obtained.

Further, the organic phase, prior to the homogenizing step, must be liquid and homogeneous. In some cases, therefore, it will be necessary to operate at a temperature sufficiently high to liquify the organic phase. Otherwise, a water-insoluble solvent which does not inhibit polymerization must be added to the organic phase in an amount just sufficient to achieve a homogeneous liquid phase. Suitable water-insoluble solvents are selected from those described above as suitable solvents for the organically-soluble initiators.

In accordance with the invention, the mixture of the organic phase containing the dispersed magnetically-charged material and the aqueous solution is homogenized at a temperature less than the decomposition temperature of the initiator to obtain organic phase droplets containing the magnetically-charged material and having a size between 0.03 and 5 microns. A vigorous mechanical means is employed to achieve homogenization. Suitable mechanical means include a colloid mill, a rapid pump, a vibrator and a ultrasonic equipment.

When the totality of the aqueous phase to be utilized in the process is not used in the homogenizing step, the minimum amount of aqueous phase is at least equal to the amount of organic phase. The remaining aqueous phase is introduced in sequential fractions or continuously, into the reaction medium before and/or during the polymerization step, described below.

Further, more organic monomeric component may be added immediately prior to or during the polymerization step, or part before polymerization and the rest during polymerization to be described below. The additional monomeric component may be added sequentially in fractions or continuously.

In accordance with the invention, the homogenized mixture is polymerized to obtain a magnetic-polymer latex containing hydrophobic polymer particles. Preferably, the finely dispersed homogenized mixture is polymerized in microsuspension in a well-known manner at temperatures between 30° and 130° C. A magnetic-polymer latex is obtained comprising less than 65% by weight hydrophobic polymer particles having diameters from 0.03 and 5 microns, preferably between 0.05 and 1 microns and a magnetically-charged material in an amount from 0.05 to 50% by weight with respect to the polymer portion of the polymer particles, the magnetically-charged material being dispersed within the polymer particles.

The polymer particles are readily attracted by a magnet even when the concentration thereof in the latex is very low. In certain applications therefore, the magnetic polymer particles may be easily separated from the ambient liquid medium without resorting to the conventional methods of coagulation and atomization.

The latices of the invention can be used in the paint industry, in magnetic tapes, in recordings, and in such applications as biological molecule substrates.

In another embodiment of the invention and in accordance therewith, the organic phase into which the magnetically-charged material is dispersed comprises an organically-soluble initiator and a water-insoluble organic compound. Suitable water-insoluble organic compounds have been described above. The water-insoluble organic compound may represent up to 50% by weight and preferably up to 20% by weight of the organic phase containing the magnetic charge.

As described above, an aqueous solution containing at least one emulsifier is prepared and mixed with the organic phase containing the dispersed magnetically-charged material. The organic phase is at least 1% of the totality of the organic phase.

The aqueous-organic phase mixture is then homogenized. An organic monomeric component, as defined above, is then added to the homogenized organic phase either before or during or before and during the above-described polymerization step. Addition of the organic monomeric component occurs either in sequential fractions or continuously. As a result of the polymerization, a magnetic-polymer latex, as described above, is obtained.

The following examples were designed to elucidate the teachings of the present invention, and in no way limit the scope of the invention. Various other modifications and equivalents of the examples will readily suggest themselves to those skilled in the art, particularly after the issuance of this patent, without departing from the spirit or scope of the present invention.

EXAMPLE 1

An organic phase is prepared by dissolving 4 g. of lauroyl peroxide in 60 g. of styrene. To this solution, are added 5 g. of a dispersion of 16% by weight of $Fe_3O_4$ in a hydrocarbon oil, the $Fe_3O_4$ having a particle size of about 0.01 microns.

An aqueous phase is prepared in an agitator-equipped container by dissolving 1 g. sodium laurylsulfate and 1 g. of oxyethylenated nonylphenol (30 ethylene oxide units per molecule) in 400 g of demineralized water.

The organic phase is then placed into and dispersed in the aqueous phase to form an organic-aqueous mixture which is homogenized at ambient temperature to obtain organic phase droplets 1 micron large which contain the magnetically-charged material and which are dispersed in the aqueous phase.

The mixture is introduced into a 1 liter reactor, provided with an agitating means, wherein polymerization takes place at 55° C.

After 19 hours the reaction medium is cooled and the residual monomer is eliminated by steam entrainment.

500 g. of a stable latex are obtained, of which the polystyrene particle concentration is 9.6% by weight. The light brown polystyrene particles have a mean diameter of 1 micron. Examination by means of an electron microscope reveals that the magnetically-charged material, which represents 1.6% by weight of the polymer, is located as inclusions along the periphery of the polystyrene particles.

The latex particles are easily separated from the medium when a magnetic attraction is present along the walls of the container. The same phenomenon is observed even when the latex is diluted to a polystyrene particle concentration of 1% by weight.

EXAMPLE 2

An organic phase is prepared which consists of:
    5.45 g. of hexadecane;
    0.80 g. of lauroyl peroxide dissolved in 2.9 g. of chlorobenzene; and
    5.45 g. of the same dispersion of $Fe_3O_4$ used in Example 1.

An aqueous phase is prepared which consists of:
    600 g. of demineralized water;
    1.6 g. of sodium laurylsulfate; and
    1.6 g. of oxyethylenated nonylphenol (30 ethylene oxide units per molecule).

As in Example 1, the organic and aqueous phases are mixed and homogenized to obtain organic phase droplets of a size of about 0.1 micron, which contain the magnetically-charged material and which droplets are also dispersed in the aqueous phase.

The organic-aqueous homogenized mixture is introduced into a 4 liter reactor, provided with an agitating means, wherein the mixture is heated to and maintained at 63° C. The moment the mixture reaches 63° C., 110 g. of distilled styrene are introduced at a constant rate over a period of 10 hours.

The mixture is left another 10 hours at 63° C.; then it is heated to 70° C. for 5 hours. Thereupon, the reaction medium is cooled.

730 g. of stable latex are obtained, of which the polymer particle concentration is 17% by weight. These particles are light brown and have a mean diameter of 0.15 microns. These particles include along their peripheries the magnetically-charged material in particle form in an amount of 0.8% by weight of the polymer. The particles are attracted by a magnet.

EXAMPLE 3

An organic phase is prepared which consists of:
    5 g. of hexadecane;
    4 g. of lauroyl peroxide dissolved in 100 g. of styrene; and
    5 g. of the same dispersion of $Fe_3O_4$ used in Example 1.

An aqueous phase is prepared which consists of:
    400 g. of demineralized water;
    1 g. of sodium laurylsulfate; and
    1 g. of oxyethylenated nonylphenol (30 ethylene oxide units per molecule).

As in Example 1, the organic and aqueous phases are mixed and homogenized to obtain organic phase droplets containing the magnetically-charged material which have a mean diameter of 1 micron and which are dispersed in the aqueous phase.

The dispersion is introduced into a 4 liter reactor, provided with an agitating means, and is heated to 60° C. and maintained at this temperature for 18 hours.

Following cooling of the reaction medium, 510 g. of stable latex are obtained, of which the polystyrene particle concentration amounts to 17% by weight.

The polystyrene particles have a light brown color and a mean diameter of 1 micron. They contain magnetically-charged material in particle form in an amount of 1.1% by weight of polymer. The magnetic particles are distributed along the peripheries of the polymer particles, which are attracted by a magnet.

EXAMPLE 4

An organic phase is prepared which consists of:
  8.6 g. of hexadecane;
  6.9 g. of lauroyl peroxide dissolved in 172.5 g. of vinyltoluene; and
  8.6 g. of the same dispersion of $Fe_3O_4$ used in Example 1.

An aqueous phase is prepared which consists of:
  690 g. of demineralized water;
  1.7 g. of sodium laurylsulfate; and
  1.7 g. of oxyethylenated nonylphenol (30 ethylene oxide units per molecule).

As in Example 1, the organic and aqueous phases are mixed and homogenized so as to obtain organic phase droplets having a mean diameter of 0.16 micron and containing the magnetically-charged material. The organic phase droplets are dispersed in the aqueous phase.

The dispersion is introduced into a 4 liter reactor, provided with an agitating means, and heated to and maintained at 60° C. for 18 hours, followed by heating at 75° C. for 2 hours.

After cooling the reaction medium, 860 g. of stable latex are obtained, having a polyvinyl toluene particle concentration of 19.7% by weight.

The polyvinyl toluene particles are light brown and have a mean diameter of 0.16 microns; they contain magnetically-charged material in particle form in an amount by weight of 0.8% of the polymer, distributed along the peripheries of the polymer particles, which are attracted by a magnet.

EXAMPLE 5

An organic phase is prepared which consists of:
  8.5 g. of hexadecane;
  6.8 g. of lauroyl peroxide dissolved in a mixture formed of 153.5 g. of styrene and 17 g. of butyl acrylate; and
  8.5 g. of the same dispersion of $Fe_3O_4$ used in Example 1.

An aqueous phase is prepared which consists of:
  683 g. of demineralized water;
  1.7 g. of sodium laurylsulfate; and
  1.7 g. of oxyethylenated nonylphenol (30 ethylene oxide units per molecule).

As in Example 1, the organic and aqueous phases are mixed and homogenized to obtain organic phase droplets having a mean diameter of 0.16 microns, containing the magnetically-charged material and being dispersed in the aqueous phase.

The dispersion is introduced into a 4 liter reactor, provided with an agitating means, and is heated to and maintained at 60° C. for 18 hours, followed by heating at 75° C. for 2 hours.

Following cooling of the reaction medium, 860 g. of stable latex are obtained, of which the concentration of styrene-butyl acrylate copolymer particles is 19.9% by weight.

The styrene-butyl-acrylate copolymer particles are light brown and have a mean diameter of 0.16 microns. The copolymer particles contain 0.8% by weight of polymer of magnetically-charged material in particle form which is distributed along the peripheries of the copolymer. These copolymer particles are attracted by a magnet.

EXAMPLE 6

An organic phase is prepared which consists of:
  7.5 g. of cetyl alcohol;
  6 g. of lauroyl peroxide dissolved in 151 g. of styrene; and
  7.5 g. of the same dispersion of $Fe_3O_4$ used in Example 1.

An aqueous phase is prepared which consists of:
  605 g. of demineralized water;
  1.5 g. of sodium lauryl sulfate; and
  1.5 g. of oxyethylenated nonylphenol (30 ethylene oxide units per molecule).

As in Example 1, the organic and aqueous phases are mixed and homogenized to obtain organic phase droplets having a mean diameter of 0.15 microns, containing the magnetically-charged material and being dispersed in the aqueous phase.

The dispersion is introduced into 4 liter reactor, provided with an agitating means. The dispersion is heated to and maintained at 60° C. for 18 hours, followed by heating at 75° C. for 2 hours.

After cooling the reaction medium, 755 g. of stable latex are obtained, having a polystyrene particle concentration of 19% by weight.

The polystyrene particles are light brown, have a mean diameter of 0.15 microns and contain magnetically-charged material in an amount of 0.8% by weight of polymer, distributed along the peripheries of the polymer particles, which are attracted by a magnet.

It will be apparent to those skilled in the art that various modifications and variations can be made without departing from the scope or spirit of the invention. Thus, it is intended that the present invention cover the modifications and variations of this invention provided they come within the scope of the appended claims and their equivalents.

We claim:
1. A magnetic-polymer latex comprising:
   (a) less than 65% by weight of hydrophobic vinyl aromatic polymer particles having a mean diameter between 0.03 and 5 microns; and
   (b) a magnetically-charged material in an amount from 0.5 to 50% by weight with respect to the polymer portion of said particles, said magnetically-charged material being dispersed within said polymer particles.

2. The latex of claim 1, wherein said hydrophobic vinyl aromatic polymer is selected from the group consisting of:
   (a) a water-insoluble vinyl aromatic homopolymer;
   (b) a copolymer consisting of water-insoluble vinyl aromatic monomers; and
   (c) a copolymer consisting of at least one water-insoluble vinyl aromatic monomer and at least one other water-insoluble copolymerizing monomer.

3. The latex of claim 2, wherein
   (1) said water-insoluble vinyl aromatic monomer homopolymer (a) consists of a monomer selected from the group consisting of styrene, alpha-methylstyrene, ethylstyrene, tert-butyl styrene and vinyl toluene;

(2) said copolymer (b) consists of water-insoluble vinyl aromatic monomers selected from the group consisting of styrene, alpha-methylstyrene, ethylstyrene, tert-butyl styrene and vinyltoluene; and (3) said copolymer (c) consists of
  (i) at least one water-insoluble vinyl aromatic monomer selected from the group consisting of styrene, alphamethyl styrene, ethylstyrene, tert-butyl styrene and vinyl toluene and
  (ii) at least one other water-insoluble copolymerizing monomer selected from the group consisting of a diene compound, an alkyl acrylate, an alkyl methacylate, an ester of ethylenic acid and alkyl.

4. A process for preparing the magnetic-polymer latex of claim 1 comprising the steps of:
  (a) dispersing a magnetically-charged material into an organic phase comprising an organically-soluble initiator and an organic monomeric component selected from the group consisting of a single vinyl aromatic monomer and a combination of a single vinyl aromatic monomer and a copolymerizing monomer;
  (b) preparing an aqueous solution comprising water and at least one emulsifier;
  (c) mixing said organic phase containing said dispersed magnetically-charged material with said prepared aqueous solution;
  (d) homogenizing said mixture of said organic phase containing said dispersed magnetically-charged material and said prepared aqueous solution; and
  (e) polymerizing said homogenized mixture to obtain a magnetic-polymer latex containing hydrophobic vinyl aromatic polymer particles.

5. The process of claim 4 wherein said organic phase in step (a) further includes a water-insoluble organic compound.

6. The process of claim 5 further including the step of adding to said homogenized mixture more of said organic monomeric compound immediately prior to or during or prior to and during the polymerization of said homogenized mixture in step (e).

7. The process of claim 4 further including the step of adding to said homogenized mixture more of said organic monomeric component immediately prior to or during or prior to and during the polymerization of said organic phase in step (e).

8. The process of claim 4, wherein said vinyl aromatic monomer is a water-insoluble monomer selected from the group consisting of styrene, alpha-methylstyrene, ethylstyrene, tert-butylstyrene and vinyltoluene.

9. The process of claim 4, wherein said copolymerizing monomer is a water-insoluble monomer selected from the group consisting of styrene, alpha-methylstyrene, ethylstyrene, tert-butyl styrene, vinyltoluene, a diene compound, an alkyl acrylate, an alkylmethacrylate, an ester of ethylenic acid and alkyl.

10. The process of claim 4, further including in said organic phase a crosslinking monomer in an amount between 0 and 5% by weight with respect to the organic monomeric component.

11. The process of claim 10 further including in said organic phase a chain-limiting agent in an amount between 0 and 5% by weight with respect to the organic monomeric component.

12. The process of claim 4 further including in said organic phase a chain-limiting agent in an amount between 0 and 5% by weight with respect to the organic monomeric component.

13. The process of claim 4 where said magnetically charged material is selected from the group consisting of a metal, a metal alloy, iron oxide, chromium dioxide, and iron oxide combined or mixed with other metal oxides.

14. The process of claim 4, wherein the size of the magnetically-charged material is less than 1 micron.

15. The process of claim 4, wherein the amount of said magnetically-charged material dispersed is between 0.5 and 50% by weight with respect to said organic monomeric component.

16. The process of claim 4, wherein said organic phase is liquid and homogeneous prior to the steps (c) and (d) of mixing and homogenizing said organic phase and said prepared aqueous solution.

17. A process for preparing the magnetic-polymer latex of claim 1 comprising the steps of:
  (a) dispersing a magnetically-charged material into an organic phase comprising an organically-soluble initiator and a water-insoluble organic compound;
  (b) preparing an aqueous solution comprising water and at least one emulsifier;
  (c) mixing said organic phase containing said dispersed magnetically-charged material with said prepared aqueous solution;
  (d) homogenizing said mixture of said organic phase containing said dispersed magnetically-charged material and said prepared aqueous solution;
  (e) adding to said homogenized mixture an organic monomeric component selected from the group consisting of a single vinyl aromatic monomer and a combination of a single vinyl aromatic monomer and a copolymerizing monomer; and
  (f) polymerizing said homogenized mixture, after said addition of said organic monomeric component, to obtain a magnetic-polymer latex containing hydrophobic vinyl aromatic polymer particles.

18. The process of claim 17 further including the step of adding more of said organic monomeric component during the step (f) of polymerizing said organic phase.

19. The process of claim 17, wherein the step (e) of adding organic monomeric component and the step (f) of polymerizing are carried out simultaneously.

20. The process of claim 5 or 17, wherein said water-insoluble organic compound is selected from the group consisting of a $C_{10-30}$ saturated aliphatic hydrocarbon, a halogenated $C_{10-30}$ saturated aliphatic hydrocarbon, a $C_{10-30}$ unsaturated aliphatic hydrocarbon, a halogenated $C_{10-30}$ unsaturated aliphatic hydrocarbon, a $C_{10-30}$ aliciclic hydrocarbon, a halogenated $C_{10-30}$ alicylic hydrocarbon, a $C_{10-30}$ aromatic hydrocarbon, a halogenated $C_{10-30}$ aromatic hydrocarbon, a saturated $C_{10-30}$ aliphatic alcohol, an unsaturated $C_{10-30}$ aliphatic alcohol, a ester of mineral acid or $C_{1-20}$ organic acid and $C_{1-20}$ alcohol.

21. The process of claim 20, wherein said esters have at least 10 carbon atoms.

22. The process of claim 17 wherein said water-insoluble organic compound represents up to 50% by weight of the organic phase containing the magnetically-charged material.

* * * * *